United States Patent [19]

Harley et al.

[11] Patent Number: 4,816,072

[45] Date of Patent: * Mar. 28, 1989

[54] DISPERSION PROCESS FOR CERAMIC GREEN BODY

[75] Inventors: A. Dale Harley, Midland, Mich.; Larwrence G. Duquette, Maynard, Mass.; Issam A. Khoury, Midland, Mich.; Iwao Kohatsu, Lexington, Mass.

[73] Assignee: The Dow Chemical Company, Midland, Mich.

[*] Notice: The portion of the term of this patent subsequent to Dec. 1, 2004 has been disclaimed.

[21] Appl. No.: 92,025

[22] Filed: Sep. 1, 1987

Related U.S. Application Data

[63] Continuation-in-part of Ser. No. 856,879, Apr. 28, 1986, Pat. No. 4,710,227.

[51] Int. Cl.$^4$ .................... C08L 1/08; C03C 3/00
[52] U.S. Cl. .................... 106/287.18; 501/12; 501/94; 501/104; 501/105; 501/108; 501/112; 501/123; 501/137; 264/63; 106/287.19
[58] Field of Search ........... 106/193; 501/12, 94, 501/104, 105, 108, 123; 264/63

[56] References Cited

U.S. PATENT DOCUMENTS

| | | | |
|---|---|---|---|
| 2,948,648 | 8/1960 | Wainer | 106/39 |
| 3,292,994 | 12/1966 | Kiss et al. | 23/51 |
| 3,330,697 | 7/1967 | Pechini | 117/215 |
| 3,413,083 | 11/1968 | Daendliker | 423/263 |
| 3,458,552 | 7/1969 | Hauck | 260/448 |
| 3,637,531 | 1/1972 | Faxon | 252/520 |
| 3,647,364 | 3/1972 | Masdiyasni | 23/51 R |
| 4,049,789 | 9/1977 | Manabe | 423/593 |
| 4,293,514 | 10/1981 | Wada | 264/61 |
| 4,361,598 | 11/1982 | Yoldas | 106/287.19 |
| 4,414,337 | 11/1983 | Ichikawa | 501/104 |
| 4,447,853 | 5/1984 | Tomuro et al. | 361/321 |
| 4,510,175 | 4/1985 | Burn | 427/79 |
| 4,710,227 | 12/1987 | Harley et al. | 106/193 |

OTHER PUBLICATIONS

Chem. Abst. 90:96712r, Suwa, 1979.
Chem. Abst. 100:113, 455d, Mitsubishi Mining, 1984.
Chem. Abst. 100:78, 476m, Kureha Chem, 1984.
Chem. Abst. 100:78, 479n, Mitsubishi Mining, 1982.
Chem. Abst. 100:149609, 1984.
Chem. Abst. 91:17,7420, Sakka, 1979.
Chem. Abst. 97:173,351, Ozaki, Y., 1982.
Chem. Abst. 94:88931, Kamiya, 1981.
Chem. Abst. 98:77085, Suwa, 1983.
Chem. Abst. 95:231028t, Yamaguchi, 1981.
Chem. Abst. 97:77322, Yamawe, 1982.

*Primary Examiner*—Theodore Morris
*Attorney, Agent, or Firm*—Barbara J. Sutherland

[57] ABSTRACT

A process is described for the preparation of a ceramic green body by hydrolyzing at least one alkoxide selected from each of two specified groups to form a dispersion of their reaction product, concentrating the dispersion to a sediment without drying it, and admixing a binder and a plasticizer with the sediment to make a ceramic slip formulation. A release agent can optionally be admixed. The slip formulation is then cast as a ceramic green body. The proportions of alkoxides can be adjusted, as desired, to produce a ceramic green body which is dielectric and useful for microcapacitors or as a conductor.

34 Claims, No Drawings

DISPERSION PROCESS FOR CERAMIC GREEN BODY

CROSS REFERENCE TO A RELATED APPLICATION

The present application is a continuation-in-part application of U.S. application Ser. No. 06/856,879, filed Apr. 28, 1986, now U.S. Pat. No. 4,710,227.

BACKGROUND OF THE INVENTION

The present invention concerns a process for making a ceramic green body of a type which can be fired into a thin ceramic sheet or tape for use in a multilayer capacitor or as a conductor.

A multilayer capacitor is a stack of a number of ceramic capacitor sheets connected in parallel to produce a capacitor of high total capacitance. These capacitors may be very small, and typically comprise between 40 and 50 ceramic sheets, each about 20 $\mu$m thick. The entire capacitor may be only about 1 mm thick. These devices fing many uses in microcircuitry.

However, there is a need for even thinner ceramic sheets or bodies, within the range of from about 3 $\mu$m to about 10 $\mu$m in thickness. This is due to the fact that equivalent capacitance could thereby be achieved using only half as many of these thinner sheets, since capacitance is inverity proportional to the thickness of the ceramic sheet. The reduction in the number of sheets would then result in a savings in material costs, because the electrode layers interspersed between the ceramic layers in a capacitor are made of expensive noble metals, and with fewer, thinner sheets, fewer electrode layers would be required. In past it has been very dificult to make sheets of this reduced thickness because current commercial methods of producing the green (unfired) sheets, also called tapes, involve processing of solides, including ceramic powders.

These ceramic powders, which are dielectric and/ar conductive, are generally dispersed into an oranic solvent such as methyl ethyl ketone/ethanol mixture. The powders are often barium titanate admixed with other compounds such as strontium titanate, lead titanate, calcium zirconate, lead oxide, borates and silicates. Ball-milling is generally necessary to maximize dispersion in the solvent, and often requires several hours at a minimum. The dispersed powders are then mixed with polymeric organic binders, plasticizers and surfactants to form a slip, which is tape-cast onto a nonporous substrate and dried in an oven to form a flexible "green tape."

To produce a capacitor, this green tape or green body is screen-printed with a noble metal electrode ink. Forty or Fifty layers, typically, of the printed tape are then laminated and, after dicing into chips or sheets, fired to burn off the organic binder. The ingoranic chips are sintered at high temperatures, typically between 1000° C. and 1400°0 C., to densify the sheets and improve their strength and conductivity. The result is a mechanically and electrically acceptable device.

A problem very commonly faced in this process, however, that tends to militate against reducing the thicknell of the sheets or tapes beyond thickness currently being produced, is the fact that ceramic powders are usually agglomerated when received and remain so to some extent even after lengthy ball-milling prior to and after dispersion in a solvent. This agglomeration makes it difficult to produce sheets of only from about 3 $\mu$m to about 10 $\mu$m in thickness that are of uniform quality, since the size and shape of the initial ceramic particles are critical factors in producing a good quality final product. This process also tends to produce sheets that exhibit loading levels that are less than optimal, and the reduced density increases the degree of shrinkage of the tape during firing. Ideally, the particles should be uniformily sized and equiaxially shaped, and should also demonstrate high purity.

Therefore, because of the problems associated with the ceramic powders and their general unsuitability to producing the thinner ceramic sheets or tapes now sought, it would be desirable to have a cermaic green body prepared from a slip fromulation which does not generally require ball-milling or other milling steps at any point and for which powder agglomeration does not present a significant problem, which exhibits good ceramic loading levels, and which therefore does not generally require processing of dry ceramic powders, with the accompanying quality problems and thickness limitations that such processing entails.

SUMMARY OF THE INVENTION

The present disclosure describes such an invention and involves an in situ finely dispersed slurry that can be used to produce a ceramic green body. Accordingly, there is provided a process comprising (a) forming a hydrolyzable solution of at least one compound of the formula $A(OR)_x$, wherein A is Be, Mg, Ca, Sr, Ba, Ge, Pb, Nd, Y, La, Pm, Sm, Eu Gd, Tb, Dy, Ho, Er, Tm, Yb, Lu, Sb, Bi, or a mixture thereof, at least one compound of the formula $B(OR)_x$, wherein B is Ti, Zr, Sc, Y, La, Nb, Fe, Ta, W, Mn, Sn, Mg, Cu, Zn, Ni, Co, Mo or a mixture thereof, wherein R is a compound characterized as $C_yH_z$ wherein y is an integer from 1 to 10, z is an integer y, 2y, 2y +1 or 2y−1, and x is independently an integer from 1 to 7, such that the compounds of the formulas $A(OR)_x$ and $B(OR)_x$ are suitable to be hydrolyzed to form a compound of the formula $ABO_{3-\Delta}$, wherein $\Delta$ is a number from 0 to 1.33, and an alcohol suitable to dissolve the compounds $A(OR)_x$ and $B(OR)_x$, (b) hydrolyzing this hydrolyzable solution to form a hydrolyzed dispersion of the compound of the formula $ABO_{3-\Delta}$ in the alcohol; (c) concentrating at least a portion of the dispersion to a sediment; (d) admixing a binder solution and a plasticizer with the sediment to make a ceramic slip formulation; and (e) preparing a ceramic green body from this slip formulation.

DESCRIPTION OF THE PREFERRED EMBODIMENTS

The process of the present invention can be advantageously used to prepare a ceramic green body from a solution without the need to use ceramic powders. The term "ceramic green body" refers to a body, often a tape or sheet, of a material that can be converted into a ceramic upon firing. The admixture and hydrolysis of soluble metal compounds of the formulas $A(OR)_x$ and $B(OR)_x$ of the appropriate stoichiometry can lead to the formation of metal oxides that have desirable properties including both insulation and conductivity.

The starting components to be utilized here typically comprise at least one compound of the formula $A(OR)_x$ and at least one compound of the formula $B(OR)_x$, each of which is generally an alkoxide adhering to the above formula. These two, or more, oompounds are hydrolyzed together and used in forming a hydrolyzed dispersion in alcohol, with which is then admixed at varying points a binder solution and a plasticizer. Optionally, a release agent can also be added. The alcohol and two groups of alkoxides form what is referred to as the "hydrolyzable solution," before hydrolysis, and afterward is referred to as the "hydrolyzed dispersion." The amounts for each of the components of the present invention have been calculated based on either the hydrolyzable solution or the hydrolyzed dispersion, as noted.

For example, the alcohol preferably comprises from about 30 to about 99 percent by weight of the hydrolyzable solution, and more preferably from about 90 to about 98 percent by weight. The alcohol is preferably selected to minimize, and more preferably avoid, the formation of insoluble alkoxide components through metathetical reactions during the herein disclosed process. Among the preferred alcohols are isopropanol, butanol, sec-butanol, pentanol and isoamyl alcohol. Isopropanol is generally more preferred here.

For the purposes of this invention, the compound adhering to the formula $A(OR)_x$ desirably comprises at least one of the metals Be, Mg, Ca, Sr, Ba, Ge, Pb, Nd, Y, La, Pm, Sm, Sb, Eu, Bi, Gd, Tb, Dy, Ho, Er, Tm, Yb, or Lu, preferably Be, Mg, Ca, Sr, Ba, Ge, Pb, Y, Sb, La, or Bi, and more preferably Pb, Y, Ca, La, Ba, Mg, Sr, and mixtures thereof. One or more selections from this group of elements is incorporated as A in the alkoxide formula $A(OR)_x$.

The compound adhering to the formula $B(OR)_x$ comprises at least one of the metals Ti, Zr, Sc, Y, La, Nb, Fe, Ta, W, Mn, Mg, Zn, Cu, Sn, Ni, Co, Mo and mixtures thereof, preferably Ti, Zr, Sc, Y, La, Nb, W, Sn, Mg, Ta, Cu or Zn, and more preferably Ti, Zr and Cu. Although it is possible to combine only one compound adhering to the formula $A(OR)_x$ with only one compound adhering to the formula $B(OR)_x$ in the present invention, the two types of compounds will be referred to herein as the first and second groups of alkoxides, respectively, since the formulas represent alkoxides as defined and groups of each can be utilized at the same time. The first and second groups of alkoxides together represent from about 1 to about 70 percent by weight of the hydrolyzable solution, and preferably from about 2 to about 10 percent by weight, the alcohol representing the remainder.

The R in both of the alkoxide formulas [$A(OR)_x$ and $B(OR)_x$] represents a compound of the general formula $C_yH_z$, wherein y is an integer from 1 to 10 and z is a integer which can be y, 2y, 2y+1 or 2y−1. The x is an integer from 1 to 7. The two groups of alkoxides are dissolved in the alcohol, and are such that they are suitable to be hydrolyzed to form a compound characterized as $ABO_{3-\Delta}$. $\Delta$ is defined as a number from 0 to about 1.33, preferably either about 0 or from about $\frac{2}{3}$ to about 5/6, depending on the desired end use of the ceramic green body. As noted above, one or both of these two groups of alkoxides can comprise mixtures of compounds employing the designated elements.

The hydrolysis of the two groups of alkoxides together is preferred and is accomplished by the addition of a greater than stoichiometric amount of water while heating at reflux temperature. This means that the amount of water to be added is preferably from about 0.5 percent to about 70 percent by weight of the hydrolyzable solution, and more preferably from about 0.5 percent to about 3.5 percent. In general, this heating is preferably of sufficient time and temperature to substantially hydrolyze the solution, and is preferably done for at least about 1 hour with continued stirring. Alkoxide solutions refluxing within the range of about 70° C. to about 110° C. are preferred, particularly when the alkoxides chosen include barium and titanium, because hydrolysis within this temperature range results in the formation of crystallites of $BaTiO_3$ having small, substantially uniform particle size in the 100Å to 2000Å range. Even more preferred are solutions refluxing within the range of from about 80° C. to about 90° C. Refluxing can be continued as long as desired, but a time within the range of about ½ hour to about 5 hours is preferred, and about ½ hour to about 1 and ½ hours is more preferred, from a standpoint of yield as well as convenience and commercial practicability.

The water is added preferably in an alcohol solution, preferably within the range of about 10 to about 50 percent water. The water and alcohol are preferably miscible at whatever percent mixed, and as already noted the alcohol for this hydrolysis is preferably selected to minimize, and more preferably to avoid, the formation of insoluble alkoxide components through metathetical reactions. The rate of addition is useful in determining the desired small particle size and reducing the possibility of undesirable agglomeration. It is therefore preferable to use a rate within the range of from about 0.2 to about 0.4 cubic centimeter per minute (cc/min), more preferably about 0.3 to about 0.35 cc/min. This latter rate helps produce particles in the 100Å to 300Å range. It is possible to increase the addition rate once an approximately stoichiometric amount of water has been added. If the water is added too rapidly at the start, however, agglomerates may form.

The hydrolysis step results in the conversion of the coordination compound formed by the first and second groups of alkoxides in the alcohol to a dispersion of the compound characterized as $ABO_{3-\Delta}$. $ABO_{3-\Delta}$ preferably comprises combinations of $BaTiO_3$ and from about 2 to about 20 mol percent of such others of the same characterization as $CaZrO_3$, $BaZrO_3$, $PbTiO_3$ and $SrTiO_3$. Other possibilities here include, for example, $CaTiO_3$, $MgTiO_3$, $SrZrO_3$, $Ba_{2/3}Y_{1/3}CuO_{7/3}$, and related compounds in which any of the designated alkoxide elements is present.

It should be noted that the $AB_3-\Delta$ system, which is the hydrolyzed dispersion, ideally displays a small particle size along with a narrow size distribution and substantial uniformity of stoichiometry between the compounds chosen from the first and second groups of alkoxides. It is preferable to use substantially stoichiometric proportions of these two groups of alkoxides to produce a body exhibiting significant dielectric characteristics. A preferred range is a ratio between the two groups of alkoxdies of about 1.1 to 1, more preferably about 1.050 to 1, and most preferably about 1.01 to 1. If dielectric properties are not of importance to a desired application, the proportionality can be correspondingly adjusted as desired. The small and uniform particle size helps to ensure uniform sintering and reduces the likelihood of flaws in the final ceramic green body.

Following the hydrolysis, it is optional to remove the excess water remaining in a separate step. For example, an azeotropic distillation of the hydrolyzed dispersion can be done such that a substantially dry alcoholic slurry results. Residual water can still be left and will not affect the final outcome as long as the water content is sufficiently low so as not to create binder solubility problems. Other drying methods including, for example, the use of drying agents such as 1,2-dimethoxy-propane, can alternatively be employed. This step is not per se necessary, however, since the subsequent concentration step, described below, serves to minimize the amount of water remaining in the final slip formulation.

A dispersant can be added at this point, preferably in the amount of from about 0.002 to about 0.5 percent by weight of the hydrolyzed dispersion, and more preferably from about 0.008 to about 0.05 percent by weight. It is alternatively possible to add it to the original alkoxide solution prior to hydrolysis, or to the hydrolyzed dispersion prior to the drying step; however, if drying is done by distillation, a substantial loss of the dispersant may result, which may in turn allow greater agglomeration afterward. Among possible dispersants are, for example, anionic dispersants such as amine salts of alkylaryl sulfonate, ethanol, polyacrylate, polymethacrylate, menhaden fish oil, and mixtures thereof. Ethanol and amine salts of alkylaryl sulfonate are preferred here, and since ethanol can also be chosen as the alcohol for the original dispersion's formation, a separate dispersant addition may be thereby obviated. The dispersant serves to increase the uniformity and reduce the agglomeration of the $ABO_{3-\Delta}$ dispersion.

While the present invention is not limited to a strict order of steps in all respects, obvious limitations will apply when it is desired to produce a mechanically and electrically acceptable device. One step preferably occurring after the hydrolysis is the concentration of the disperse, or internal, phase to a nonisolated sediment in a greatly reduced volume of the continuous, or external, phase. The remaining volume of the continuous phase, which is primarily alcohol, is ideally just sufficient to maintain the $ABO_{3-\Delta}$ dispersion in a nonagglomerated state. Experimentally, the state of the $ABO_{3-\Delta}$ dispersion was determined essentially visually. The amount of continuous phase remaining can be determined, for example, by measuring either the volume of distillate collected during the drying/concentration step or the liquid content of the sedimentation volume following gravimetric settling or centrifugation.

Centrifugation provides one effective means of concentration without complete isolation from the continuous phase and is the preferred method. Other means can include distillation, decantation (gravitational sedimentation), or oombinations of these procedures. Complete isolation, i.e., drying of the sediment, at any point should be avoided both because of the undesirable agglomeration that will result and because of the difficulty of redispersing the formulation if it has dried. An important point of this invention, as already noted, is that the formulation remains as a slurry throughout the processing.

Another important point to the present invention is that it employs a binder solution. The binder serves to help disperse the solids and to stabilize the suspension, and also provides integrity and strength to the final product. If concentration is by distillation, the binder solution can be added prior to concentration, provided that the dispersion, or suspension, is sufficiently water-free. However, in general, and especially in the cases of concentration by centrifugation and by gravitational settling, addition of the binder solution after concentration minimizes the loss of binder in the discarded external phase.

The solvent employed for the binder can be aqueous or nonaqueous, with the solvent choice obviously depending on the binder choice. Examples of possible solvents include toluene, methyl ethyl ketone, methanol or a methanol/water mixture, with toluene being preferred. If an organic-based system is chosen, ethylcellulose makes an excellent binder. Other organic binder systems are those using ethyl hydroxyethyl cellulose and polyacrylic acid esters. For a water-based system, polymers such as methylcellulose, hydroxypropyl ethylcellulose, hydroxybutyl methylcellulose, carboxymethylcellulose, hydroxyethylcellulose, polyvinylalcohols, polyvinylpyrrolidones, poly(acrylic acid), polyacrylamide, polyethylene oxides and mixtures of these polymers can be employed as binders in formulating the slip. The cellulose ethers are preferred binders, and more preferred here is water-soluble methylcellulose. An aqueous binder system obviates the need to substantially remove water from the hydrolyzed dispersion.

The use of these and related binders will help to form a very uniform slip that upon casting forms a thin transparent film, indicating good uniformity of metal oxide particulates and binder particulates. The particulates range from 100Å to 2000Å in size. The binder solvent represents preferably from about 1 to about 6 percent by weight of the hydrolyzed dispersion, and more preferably from about 2 to about 4 percent by weight. The binder itself is preferably from about 0.1 to about 5 percent by weight, and more preferably from about 0.1 to about 1 percent by weight.

A release agent, such as a polyol, mineral oil, or mixture thereof, can also optionally be added to the binder solution prior to adding the solution to the dispersion. This serves to facilitate easy stripping of the green tape from the casting substrate. When using a glass substrate, 1,2,4-butanetriol makes an excellent release agent. Nonglass substrates, such as polypropylene, can also be used while employing other release agents. The release agent preferably amounts to from about 0.01 to about 5 percent by weight of the hydrolyzed dispersion, and more preferably from about 0.05 to about 3 percent by weight.

In the present invention, a plasticizer is also employed and serves to lower the glass transition point of the binder to ambient or room temperature to increase the flexibility of the film, thereby making the green body or tape more easily removed from the substrate and more suitable for lamination. Examples of typical plasticizers include dimethyl formamide and propylene glycol, both of which are particularly effective in a methylcellulose aqueous solution, and dioctyl phthalate and benzyl butyl phthalate, both of which work well in an ethylcellulose organic-based system. For an ethylcellulose binder solution, dioctyl phthalate and benzyl butyl phthalate are preferred plasticizers. The plasticizer is added preferably in an amount of from about 0.01 to about 5 percent by weight of the hydrolyzed dispersion, and more preferably from about 0.05 to about 3 percent by weight.

It is preferable when adding the binder solution containing the plasticizer and, if desired, release agent to the $ABO_{3-\Delta}$ dispersion to use some means to keep the viscosity of the dispersion as low as possible. This can be done both during and after the addition of the binder. Means such as the use of appropriate commercially available surfactants can be employed when necessary to avoid agglomeration.

The final component of the slip formulation is optionally one or more sintering aids. For these, preferably low-melting eutectic oxide mixtures can be employed, including compounds such as $GeO_2$, $B_2O_3$, $PbO$, $Bi_2O_3$, $TiO_2$, $Sb_2O_3$, $SnO$, $SiO_2$ and mixtures thereof, preferably $GeO_2$, $B_2O_3$, $PbO$, $Bi_2O_3$, $Sb_2O_3$, $SnO$, and mixtures thereof. There are various ways in which one or more of these can be added so that they can perform their function of densifying the ceramic film and thereby increasing its strength and dielectric properties. In one preferred embodiment a third group of alkoxides of a type that will form sintering aids, such as glass frits, upon hydrolysis is selected. At least one compound of this group is then hydrolyzed in alcohol either concurrently with the first and second groups of alkoxides, in a step-wise fashion before or after the hydrolysis of the first and second groups, or entirely separately from the first and second groups. In the latter case the eutectic oxide mixture can be added at any subsequent point in the process of the present invention, such as prior to or after concentration or along with the addition of binder solution, plasticizer, optional release agent and so forth. Alternatively, the sintering aid to be employed can be purchased commercially, obviating the need for hydrolyzing a third group of alkoxides. The amount used represents from about 0.01 to about 2 percent by weight of the hydrolyzed dispersion, and preferably from about 0.03 to about 0.2 percent by weight. To further augment the dielectric properties of the final film, dopants that will form $MnO$, $Mn_2O_3$, $CoO$, or $Co_2O_3$ can also be added, but they are not necessary to the present invention.

The last step of this process involves the conversion of the uniform concentrated dispersion into a ceramic green body using known methods, such as curtain-coating, tape-casting or doctor-blading. It is preferred to tape-cast a single layer of the nonisolated dispersion sediment onto a nonporous substrate. The techniques for converting slip formulations into flexible green tapes are well known. For example, see the chapter "Tape-Casting of Ceramics" in *Ceramic Processing Before Firing*, edited by G. Y. Onada, Jr. and L. L. Hench, John Wiley and Sons, Inc., N.Y. (1978), pp. 411–447.

The green body prepared according to the process of the present invention can then be converted using known methods into a thin ceramic sheet or tape. Typically, the green body is calcined to burn off the polymer and to convert the tape or sheet to a ceramic material. This is then sintered, or fired, at a temperature of from 1000° C. to 1400° C. Advantageously, the green body of the present invention exhibits a good loading level which tends to reduce shrinkage upon firing. Preferably, the fired ceramic sheets, which can also be called films, of the present invention range from about 1 $\mu$m to about 50 $\mu$m in thickness, more preferably from about 3 $\mu$m to about 10 $\mu$m. They can be employed in the preparation of capacitors or conductors which have a reduced volume compared to many known capacitors or conductors due to the increased capacitance of the thinner sheets. Thus, these capacitors may be less expensive to produce than many known capacitors because they require fewer noble metal electrode layers.

It should be noted that steps necessary to the present invention, regardless of order taken, include the preparation of a hydrolyzed dispersion of at least one compound from each of the first and second groups of alkoxides, provided hydrolysis of these two groups occurs together, the concentration of the dispersion, and the addition of binder solution and plasticizer to make a slip formulation to be used in preparing a ceramic green body. The order of addition of the binder solution, plasticizer and optional release agent can be varied. As noted, for example, the binder solution, plasticizer and optional release agent, or any combination thereof, can be added prior to the concentration, although it is preferable to add these after the concentration to minimize their loss in any discarded external phase. The optional dispersant cannot be added before the hydrolysis, but can be added either before or after an optional drying step. Hydrolysis itself can be done in more than one step, with a third group of alkoxides hydrolyzed in order to supply the optional sintering aids, and then the first and second groups of alkoxides added for a second hydrolysis, for example, or in reverse order. Other variations in order are also possible, including having more than one addition step for a given component, as long as the weight percent ranges are satisfied. As noted, commercial sintering aids can alternatively be used and dispersed at various points in the process.

The following examples are given to illustrate the present invention and are not intended to be, nor should they be construed as being, limitative in any way of the scope of the invention. All parts and percentages are by weight unless otherwise indicated.

EXAMPLE 1

About 6.2 g (0.0218 mole) of titanium isopropoxide [$Ti(i-C_3H_7O)_4$], 6.8 g (0.0215 mole) of barium isopropoxide isopropylate [$Ba(i-C_3H_7O)_2C_3H_7OH$, and 150 ml of isopropanol are added to a 500 ml Schlenk flask in a dry box. The admixture is refluxed over argon for 30 minutes to produce a colorless solution.

A solution of 5 ml water and 5 ml isopropanol is then added to the refluxing solution at the rate of about 0.2 ml/min. The water/isopropanol solution has been degassed previously. The addition is made via a 1/16"(0.16 cm) cannular tube and the solution is continually stirred during the addition. At this point the reaction mix shows a dispersion of finely divided white particles. Refluxing is continued for about 2 hours, and the solution is allowed to cool naturally.

The final product, a milky dispersion, is then allowed to sit in a graduated cylinder at room temperature. There is produced a gravitational sediment volume of 25 ml in which is estimated to be about 3.2 g of $BaTiO_3$.

The XRD (x-ray diffraction) pattern of the settled $BaTiO_3$ shows an average crystallite diameter of 110Å which would correspond to a surface area of about 91 $m^2/g$. TEM (Transmission Electron Microscopy) shows primary particles (spheres) measuring about 185Å in diameter.

To a mechanically stirred gravitational sediment volume of this $BaTiO_3$ (3.2 g/25 cc) prepared in the above manner is added dioctyl phthalate, 0.3 g, as a plasticizer, and 1,2,4-butanetriol, 0.3 g, as a release agent. This dispersion is stirred at 300 rpm for 10 minutes and 0.8 g of ETHOCEL* 45 brand ethylcellulose is added over a 30 minute period, as a binder. (*ETHOCEL is a trademark of The Dow Chemical Company.) Stirring is then continued an additional 1.5 hours. One ml of a 0.6 percent by weight solution of an amine salt of alkylaryl sulfonate in isopropanol is then added as a dispersant.

An 8.0 mil thick film is cast on glass using a doctor-blade. The film is dried at room temperature in air to produce a translucent 0.7 mil film that is easily stripped from the glass surface. X-ray powder diffraction line broadening measurements of this film show an average crystallite size of 133Å. STEM (Scanning Transmission Electron Microscopy) photos show slightly agglomerated particles with an average primary particle diameter of 200Å. Thermogravimetric analysis of the film gives a ceramic content of the film of about 67 percent by weight.

EXAMPLE 2

Ba(i-C$_3$H$_7$O)$_2$ (4.63 g, 0.0182 mole), Sr(i-C$_3$H$_7$O)$_2$ (0.71 g, 0.0034 mole), Ti(i-C$_3$H$_7$O)$_4$ (5.92 g, 95 percent in isopropanol, 0.0197 mole), Zr(n-C$_3$H$_7$O)$_4$ (0.75 g, 95 percent in isopropanol, 0.0022 mole) and Pb(i-C$_3$H$_7$O)$_2$ (0.14 g, 4.3×10$^{-3}$ mole) are dissolved in 250 ml of dried and deoxygenated isopropanol. The solution is added to a stirred reaction vessel under an inert atmosphere and refluxed for about 45 minutes. A 10 percent by volume solution of distilled water in isopropanol, as a solvent, is added at a rate of about 0.3 ml/min, until a volume of 35 ml is added. The addition rate is then increased to 3 ml/min until a total volume of 100 ml has been delivered. Reflux is continued an additional 1.5 hours during which hydrolysis is substantially completed.

The water is removed by azeotropic distillation and the suspension is then concentrated by centrifuging at 40 G until a bed volume of 25 ml is obtained. The non-isolated product is estimated to weigh about 5 g and analysis shows it to have the nominal composition: BaTiO$_3$, 71.77 percent; SrTiO$_3$, 12.23 percent; BaZrO$_3$, 11.56 percent: TiO$_2$, 0.58 percent: and PbO, 3.85 percent.

ETHOCEL 45 ethylcellulose, 1 g, is dissolved in 10 ml of toluene and 1 ml of ethanol, and 0.3 g of dioctyl phthalate and 0.7 g of propylene glycol are added. The solution is then added to the centrifugate and the mixture stirred for about 2 hours. The resultant slip has a viscosity of about 400 centipoise. The slip is then cast by doctor-blade at 5 and 10 mil thicknesses, resulting in transparent dried films of 0.7 and 1.5 mil thicknesses, respectively. Laminates of 10 layers of the films pressed at 250° C. and 1500 psi are translucent and have a ceramic content of about 71.5 weight percent.

EXAMPLE 3

Ethanol/isopropanol (5 ml/300 ml) is placed in a 500 ml Schlenk flask which is attached to a Soxhlet extraction system. The set-up has been degassed and pressurized with argon three times. While under a positive pressure of argon, there is placed into the Soxhlet chamber a glass thimble with 10 g (0.25 mole) of 99.5 percent calcium granules.

Refluxing of the ethanol/isopropanol is commenced under a blanket of argon. The reaction is not vigorous. The system has been vented slightly for the escape of generated hydrogen. After refluxing for 1 week, there remains in the glass thimble a considerable amount of greyish-white powder, believed to be CaO (hydrolysis product of calcium alkoxide). The adventitious water has entered the system via the ethanol that is used. In the reaction pot is dispersed a trace amount of the CaO which is filtered off in an inert atmosphere. The filtration is done through a fine glass frit (4–5.5μ), for a time of about 6 hours. The filtrate is subjected to a vacuum for about 15 hours, producing about 27 g of a cream-colored powder.

Analysis (plasma emission) of a 2.5 percent isopropanol solution of the filtrate shows the solid to be Ca[OCH(CH$_3$)$_2$]$_2$ contaminated with about 10 percent Ca(OCH$_2$CH$_3$)$_2$.

About 3.81 g of zirconium n-propoxide propylate, about 1.64 g of a 90 percent solution of calcium isopropoxide prepared as described above, and about 300 ml of isopropanol are added to a 500-ml Schlenk flask. The mix is refluxed under an argon atmosphere for 30 minutes to give a slightly yellow solution.

To this refluxing solution is added (at a rate of about 0.2 ml/min) with stirring a degassed solution of about 2.5 ml H$_2$O/isopropanol. The addition is done via a 1/16 inch (0.16 cm) cannular tube and stirring is continued about a half hour. Following completion of the addition the reaction mixture of finely dispersed white particles continues to be refluxed for about 2 hours.

The product (a milky dispersion) is then allowed to sit at room temperature in a graduated cylinder for about 3 days. After this time a gravitational sediment volume of about 35 ml with about 4.4 percent CaZrO$_3$ was present. On centrifuging the volume is reduced to 14 ml and is a dispersion comprising about 10 percent CaZrO$_3$. Microscopic analysis reveals agglomerates as large as about 25 μm.

An XRD of the centrifuged sediment calcined to 900° C. for 2 hours produces a pattern showing the presence of CaZrO$_3$ and ZrO$_2$. Analysis (plasma emission) shows a Ca/Zr atomic ratio of about 1.00/1.14.

A ceramic green body is slip cast to tape by the procedure of Example 2.

EXAMPLE 4

After hand mixing the centrifuged sediment volumes of BaTiO$_3$/isopropanol (4 g/12 ml) and CaZrO$_3$/isopropanol (1 g/12 ml) as described in Example 3, about 6 ml of 12.5 percent ETHOCEL 45/ isopropanol solution is added. While continually stirring the dispersion (at a rate of about 300 rpm), dioctylphthalate (0.73 g) and 1,2,4-butanetriol (0.73 g) are also added. After an additional 30 minutes of stirring, there are added about 6 drops of a 0.6 percent solution of the emulsifier in isopropanol. Microscopic analysis of the product reveals a glassy mass of particles of about 2.5 μm with some agglomerates of about 15 μm.

An 8ml slip is cast and dried at room temperature to give a slightly cloudy film which is difficult to strip from a glass substrate. A TGA shows a 66 percent solid ceramic film content. An XRD of the powdered film shows only the BaTiO$_3$ pattern with an average particle diameter of about 115Å. The CaZrO$_3$ present does not exhibit an XRD pattern A tablet is pressed out of the powdered film, calcined up to about 850° C., and then sintered at about 1310° C. for about 1½ hours. A surface XRD of the sintered tablet shows the presence of [BaCa] [TiZr]O$_3$ STEM photos of both a fracture and surface of the tablet show some pores, but look fairly dense overall, estimated at about 85 to 90 percent dense.

EXAMPLE 5

According to the procedure of Example 2, the following ratios of reactants are admixed in 500 ml of dry and deoxygenated isopropanol: Ba(i-C$_3$H$_7$O)$_2$ (9.28 g, 0.0363 mole); Y(i-C$_3$H$_7$O)$_3$ (4.84 g, 0.0182 mole): and Cu(C$_2$H$_5$O)$_2$ (8.38 g, 0.0546 mole). The solution is stirred and refluxed for 45 minutes at which time the mixture is hydrolyzed as in Example 2. The hydrolysis results in the formation of a dispersion of a solid powder having the nominal composition of Ba$_{2/3}$Y$_{1/3}$CuO$_3$−Δ, such that 3−Δ=2.167 to 2.33. The dispersion can be concentrated, admixed with a binder solution and a plasticizer to make a slip formulation, and cast as a ceramic green body as described in Example 2. After appropriate firing, the resultant ceramic body has utility as a conductive material.

What we claim is:

1. A process for preparing a ceramic green body comprising:
   (a) forming a hydrolyzable solution of at least one compound of the formula $A(OR)_x$, wherein A is Be, Mg, Ca, Sr, Ba, Ge, Pb, Nd, Y, La, Pm, Sm, Eu, Gd, Tb, Dy, Ho, Er, Tm, Yb, Lu, Sb, Bi or a mixture thereof,
   at least one compound of the formula $B(OR)_x$, wherein B is Ti, Zr, Sc, Y, La, Nb, Fe, Ta, W, Mn, Sn, Mg, Cu, Zn, Ni, Co, Mo or a mixture thereof,
   wherein R is a group of the formula $C_yH_z$ wherein y is an integer from 1 to 10,
   z is an integer y, 2y, 2y+1 or 2y−1, and
   x is independently an integer from 1 to 7,
   such that said compounds of the formulas $A(OR)_x$ and $B(OR)_x$ are suitable to be hydrolyzed to form a compound of the formula $ABO_{3-\Delta}$, wherein $\Delta$ is a number from 0 to 1.33,
   and an alcohol suitable to dissolve said compounds of the formulas $A(OR)_x$ and $B(OR)_x$;
   (b) hydrolyzing said hydrolyzable solution to form a hydrolyzed dispersion of said compound of the formula $ABO_{3-\Delta}$ in said alcohol;
   (c) concentrating at least a portion of said dispersion to form a sediment;
   (d) admixing a binder solution and a plasticizer with said sediment to make a ceramic slip formulation; and
   (e) preparing a ceramic green body from said slip formulation.

2. The process of claim 1 wherein said hydrolyzable solution is hydrolyzed by adding water in an amount from about 0.5 percent to about 70 percent by weight of said hydrolyzable solution.

3. The process of claim 1 wherein said compound of the formula $A(OR)_x$ and said compound of the formula $B(OR)_x$ are hydrolyzed together.

4. The process of claim 1 wherein the hydrolysis is conducted by adding water to the hydrolyzable solution at a rate of from about [0.2 cc/min.] 0.012 percent of total volume of the hydrolazable solution per minute to about [0.4 cc/min] 0.26 percent of the total volume of the hydrolyzable solution per minute.

5. The process of claim 1 wherein A is Mg, Ca, Sr, Ba, Y, La, or Pb.

6. The process of claim 1 wherein B is Ti, Zr, Sc, Y, La, Nb, Ta, W, Sn, Mg, Cu or Zn.

7. The process of claim 1 wherein said alcohol comprises from about 30 to about 99 percent by weight of said hydrolyzable solution.

8. The process of claim 1 wherein said hydrolyzable solution comprises in total from about 1 to about 70 percent by weight of compounds of the formulas $A(OR)_x$ and $B(OR)_x$.

9. The process of claim 1 wherein from about 0.002 to about 0.5 percent by weight of a dispersant is admixed with said hydrolyzed dispersion or said sediment.

10. The process of claim 9 wherein said dispersant is selected from the group consisting of ethanol, polyacrylate, polymethacrylate, amine salts of alkyaryl sulfonate, menhaden fish oil, and mixtures thereof.

11. The process of claim 1 wherein a release agent is admixed with said hydrolyzed dispersion or said sediment.

12. The process of claim 10 wherein said release agent is in an amount of from about 0.01 percent to about 5 percent by weight of said hydrolyzed dispersion.

13. The process of claim 10 wherein said release agent is selected from the group consisting of a polyol, mineral oil, or mixtures thereof.

14. The process of claim 12 wherein said release agent is 1,2,4-butanetriol.

15. The process of claim 1 wherein said binder solution comprises from about 0.1 to about 5 percent by weight of said hydrolyzed dispersion.

16. The process of claim 15 wherein said binder solvent comprises from 1 to 6 percent by weight of said hydrolyzed dispersion.

17. The process of claim 15 wherein said binder is selected from the group consisting of ethylcellulose, methylcellulose, ethyl hydroxyethyl cellulose, and mixtures thereof.

18. The process of claim 1 wherein said plasticizer comprises from 0.01 to 5 percent by weight of said hydrolyzed dispersion.

19. The process of claim 1 wherein said plasticizer is selected from the group consisting of dioctyl phthalate, dimethyl formamide, benzyl butyl phthalate, propylene glycol, and mixtures thereof.

20. The process of claim 1 wherein said hydrolyzed dispersion comprises excess water.

21. The process of claim 20 wherein said excess water is substantially removed prior to admixing said binder solution.

22. The process of claim 21 wherein said excess water is substantially removed by means of azeotropi distillation.

23. The process of claim 21 wherein said excess water is substantially removed by means of a drying agent.

24. The process of claim 1 wherein said slip formulation comprises a sintering aid.

25. The process of claim 24 wherein said sintering aid comprises a low-melting eutectic oxide mixture.

26. The process of claim 24 wherein said sintering aid is prepared by hydrolysis of a suitable alkoxide.

27. The process of claim 25 wherein said alkoxide comprises from about 0.01 percent to about 2 percent by weight of said hydrolyzed dispersion.

28. The process of claim 1 wherein said ceramic green body is from about 1 μm to about 50 μm in thickness.

29. The process of claim 1 wherein said ceramic green body is from about 3 μm to about 10 μm in thickness.

30. The process of claim 1 wherein said compounds of the formulas $A(OR)_x$ and $B(OR)_x$ are used in a ratio of from about 1 to 1 to about 1.1 to 1.

31. The process of claim 1 wherein said compounds of the formulas $A(OR)_x$ and $B(OR)_x$ are used in a ratio of about 1 to 1.

32. The process of claim 1 wherein said $\Delta$ has a value of about 0.

33. The process of claim 1 wherein said $\Delta$ has a value of from about ⅔ to about 5/6.

34. A process for preparing a ceramic green body comprising:
   (a) forming a hydrolyzable solution of at least one compound of the formula $A(OR)_x$, wherein A is Be, Mg, Ca, Sr, Ba, Ge, Pb, Nd, Y, La, Pm, Sm, Eu, Gd, Tb, Dy, Ho, Er, Tm, Yb, Lu, Sb, Bi or a mixture thereof,
   at least one compound of the formula $B(OR)_x$, wherein B is Ti, Zr, Sc, Y, La, Nb, Fe, Ta, W, Mn, Sn, Mg, Cu, Zn, Ni, Co, Mo or a mixture thereof,
   wherein R is a group of the formula $C_yH_z$ wherein y is an integer from 1 to 10,
z is an integer y, 2y, 2y+1 or 2y−1, and
such that said compounds of the formula $A(OR)_x$ and $B(OR)_x$ are suitable to be hydrolyzed to form a compound of the formula $ABO_{3-\Delta}$, wherein $\Delta$ is a number from 0 to 1.33,
x is independently an integer from 1 to 7,
and an alcohol suitable to disolve said compounds of the formula $A(OR)_x$ and $B(OR)_x$;

(b) hydrolyzing said hydrolable solution to form a hydrolyzed dispersion of said compound of the formula $ABO_{3-\Delta}$ in said alcohol;

(c) incorporating a binder solution and a plasticizer and concentrating said hydrolyzed dispersion to make a ceramic slip formulation; and (d) preparing a ceramic green body from said ceramic slip formulation.

* * * * *

UNITED STATES PATENT AND TRADEMARK OFFICE
CERTIFICATE OF CORRECTION

PATENT NO. : 4,816,072           Page 1 of 3

DATED : March 28, 1989

INVENTOR(S) : A. Dale Harley, et al.

It is certified that error appears in the above-identified patent and that said Letters Patent is hereby corrected as shown below:

Column 1, line 22 please delete "fing" and insert -- find --.

Column 1, line 28 please delete "inverity" and insert -- inversely --.

Column 1, lines 34-35 please delete "In past it has been very dificult" and insert -- In the past it has been very difficult --.

Column 1, line 39 please delete "and/ar" and insert -- and/or --.

Column 1, line 40 please delete "oranic" and insert -- organic --.

Column 1, line 41 please delete "as methyl" and insert -- as a methyl --.

Column 1, line 56 please delete "ingoranic" and insert -- inorganic --.

Column 1, line 58 please delete "$1400°0$ C" and insert -- $1400°C$ --.

Column 1, line 63 please delete "thicknell" and insert -- thickness --.

Column 1, line 63 please delete "thickness" and insert -- thicknesses --.

Column 2, line 8 please delete "uniformily" and insert -- uniformly --.

Column 2, line 13 please delete "cermaic" and insert -- ceramic --.

Column 2, line 14 please delete "fromulation" and insert -- formulation --.

Column 2, line 67 please delete "oompounds" and insert -- compounds --.

Column 3, line 49 please delete "a" and insert -- an --.

Column 4, line 44 please delete "$AB_3-\Delta$" and insert -- $ABO_{3-\Delta}$ --.

Column 4, line 53 please delete "alkoxdies" and insert -- alkoxides --.

Column 4, line 54 please delete "1.050" and insert -- 1.05 --.

Column 5, line 44 please delete "oombinations" and insert -- combinations --.

Column 6, line 67 please delete "$SiO_2$" and insert -- $SiO_2$, --.

UNITED STATES PATENT AND TRADEMARK OFFICE
CERTIFICATE OF CORRECTION

PATENT NO. : 4,816,072

DATED : March 28, 1989

INVENTOR(S) : A. Dale Harley, et al.

It is certified that error appears in the above-identified patent and that said Letters Patent is hereby corrected as shown below:

Column 7, line 3 please delete "funotion" and insert -- function --.

Column 7, line 24 please delete "oan" and insert -- can --.

Column 7, line 29 please delete "ourtain-coating" and insert -- curtain-coating --.

Column 7, line 56 please delete "elecotrode" and insert -- electrode --.

Column 8, line 26 please delete "[Ba(i-$C_3H_7O)_2C_3H_7$OH" and insert -- [Ba(i-$C_3H_7O)_2C_3H_7$OH] --.

Column 10, line 23 please delete "prooedure" and insert -- procedure --.

Column 10, line 44 please delete "pattern" and insert -- pattern. --.

Column 10, line 48 please delete "[TiZr]$O_3$" and insert -- [TiZr]$O_3$. --.

Column 11, line 41 please delete "[0.2 cc/min.]".

Column 11, line 42 please delete "hydrolazable" and insert -- hydrolyzable --.

Column 11, line 43 please delete "[0.4 cc/min]".

Column 11, line 61 please delete "alkyaryl" and insert -- alkylaryl --.

Column 12, line 29 please delete "azeotropi" and insert -- azeotropic --.

Column 13, line 2 please delete ", and" and insert -- , and x is independently an integer from 1 to 7, --.

Column 13, line 7 please delete "x is independently an integer from 1 to 7,".

Column 13, line 8 please delete "disolve" and insert -- dissolve --.

Column 13, line 9 please delete "formula" and insert -- formulas --.

UNITED STATES PATENT AND TRADEMARK OFFICE
CERTIFICATE OF CORRECTION

PATENT NO. : 4,816,072

DATED : March 28, 1989

INVENTOR(S) : A. Dale Harley, et al.

It is certified that error appears in the above-identified patent and that said Letters Patent is hereby corrected as shown below:

Column 14, line 1 please delete "hydrolable" and insert -- hydrolyzable --.

Signed and Sealed this

Fifth Day of December, 1989

*Attest:*

JEFFREY M. SAMUELS

*Attesting Officer*  *Acting Commissioner of Patents and Trademarks*